United States Patent [19]

Spelman et al.

[11] Patent Number: 5,800,500
[45] Date of Patent: Sep. 1, 1998

[54] COCHLEAR IMPLANT WITH SHAPE MEMORY MATERIAL AND METHOD FOR IMPLANTING THE SAME

[75] Inventors: Francis A. Spelman, Seattle; Ben M. Clopton, Bainbridge Island; Arne Voie, Seattle, all of Wash.; Claude N. Jolly, Axams, Austria; Ky Huynh, Tigard, Oreg.; Jerome Boogaard, Forest Grove, Oreg.; John W. Swanson, Portland, Oreg.

[73] Assignees: PI Medical Corporation, Portland, Oreg.; University of Washington, Seattle, Wash.

[21] Appl. No.: 858,473

[22] Filed: May 20, 1997

Related U.S. Application Data

[63] Continuation-in-part of Ser. No. 516,861, Aug. 18, 1995, Pat. No. 5,630,839.

[51] Int. Cl.[6] .................................................. A61N 1/05
[52] U.S. Cl. ................................................... 607/137
[58] Field of Search ..................................... 607/137

[56] References Cited

U.S. PATENT DOCUMENTS

| | | | |
|---|---|---|---|
| 4,261,372 | 4/1981 | Hansen et al. | 128/784 |
| 4,284,085 | 8/1981 | Hansen et al. | 128/784 |
| 4,648,403 | 3/1987 | Van Compernolle | 128/419 |
| 4,686,765 | 8/1987 | Byers et al. | 29/858 |
| 4,741,339 | 5/1988 | Harrison et al. | 128/419 |
| 4,762,135 | 8/1988 | van der Puije et al. | 128/784 |
| 4,809,712 | 3/1989 | Kuzma | 128/784 |
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 4,961,434 | 10/1990 | Stypulkowski | 128/784 |
| 5,000,194 | 3/1991 | Van den Honert et al. | 128/784 |
| 5,042,084 | 8/1991 | Daly | 455/41 |
| 5,178,957 | 1/1993 | Kolpe et al. | 428/458 |
| 5,232,549 | 8/1993 | Cathey et al. | 456/633 |
| 5,336,636 | 8/1994 | Burmer | 437/173 |
| 5,515,848 | 5/1996 | Corbett, III et al. | 128/642 |
| 5,524,338 | 6/1996 | Martyniuk et al. | 29/825 |

FOREIGN PATENT DOCUMENTS

| | | | |
|---|---|---|---|
| 0 215 726 | 3/1987 | European Pat. Off. | A61N 1/40 |
| 0 329 112 | 7/1989 | European Pat. Off. | A61N 1/05 |
| 2 403 084 | 2/1984 | France | A61N 11/04 |
| WO 93/06698 | 11/1993 | WIPO | A61F 2/18 |
| WO 94/00088 | 8/1994 | WIPO | A61F 11/04 |
| WO 94/00088 | 9/1994 | WIPO | A61F 11/04 |
| WO 97/06760 | 2/1997 | WIPO | A61F 11/04 |
| WO 97/06760 | 5/1997 | WIPO | A61F 11/04 |

OTHER PUBLICATIONS

Rubinstein, J.T., et al., "Current Density Profiles of Surface Mounted and Recessed Electrodes for Neural Prostheses," Reprinted from *IEEE Transactions on Biomedical Engineering*, vol. BME–34, No. 11 (Nov. 1987).

*Primary Examiner*—William E. Kamm
*Attorney, Agent, or Firm*—Chernoff, Vilhauer, McClung & Stenzel, LLP

[57] ABSTRACT

A multi-electrode cochlear implant is taught in which approximately twenty or more insulated metal wires are wound around a flexible tube. These wires are held in place with a further layer of dielectric insulating material. The insulation is selectively removed with a laser beam to form electrodes. Two or more layers or valences of wires can be used, with the inner layer of wires terminating distal to the outer layers to provide a stepwise approximation of the tapering of the scala tympani. A shape memory material core may be introduced into the tube, so that the implant will retain an effective shape after implantation. In a preferred embodiment, electrical conductors are connected to the shape memory material to permit the select warming of the shape memory material by the passing of an electric current through it. In an alternative preferred embodiment, the shape memory material is warmed by adjacent heating elements.

15 Claims, 4 Drawing Sheets

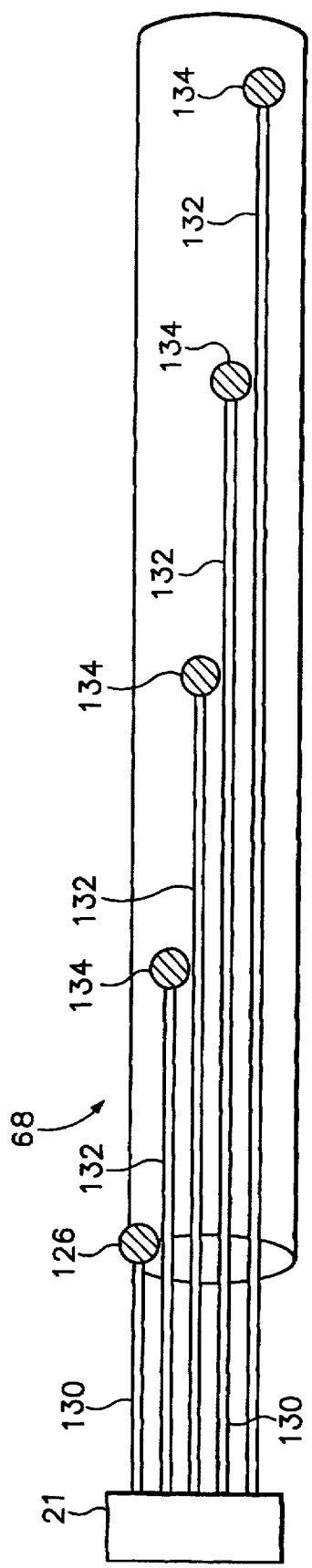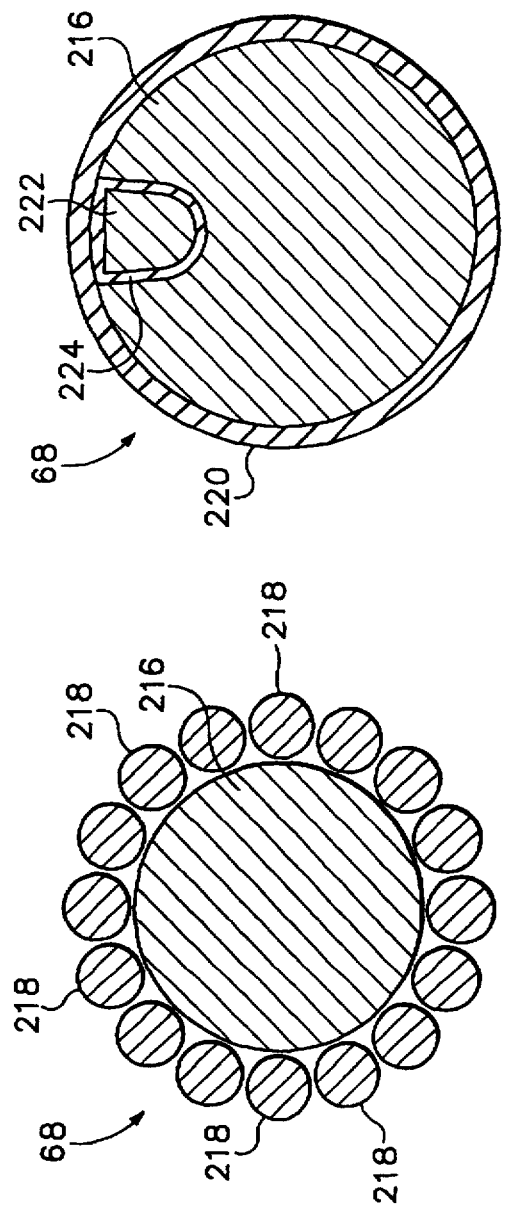

COCHLEAR IMPLANT WITH SHAPE MEMORY MATERIAL AND METHOD FOR IMPLANTING THE SAME

This application is a continuation-in-part of application Ser. No. 516,861, filed Aug. 18, 1995, now U.S. Pat. No. 5,630,839.

This invention was made with government support under grant 1 R41DCO2424-01 and 1 R42DC/NS02424-02 awarded by the National Institutes of Health. The government has certain rights in the invention.

BACKGROUND OF THE INVENTION

The present invention relates to a cochlear implant. More specifically it relates to a cochlear implant with an increased density and improved quality of electrodes and having physical characteristics which allow it to be placed into a more complete and more effective contact with the cochlea.

Most cases of profound hearing loss may be successfully addressed by a prosthesis that induces the electrical stimulation of the cochlea in response to sound received by a nearby microphone. (The cochlea is an organ of the inner ear, shaped like a snail, in which the auditory neurons have their receptive terminus.) Great efforts have been made over the last thirty years to address profound hearing loss in this manner.

The cochlea includes an electrolyte-solution-filled cavity shaped in the form of a tapering helix, known as the scala tympani. The receptive auditory neurons reside close to the interior or modiolar wall of this cavity. These neurons may be stimulated by the application of electrical potential gradients to this wall.

The range and utility of the prosthetic hearing realized depends on the accuracy and precision with which potential gradients can be applied to this wall. The task of producing potential gradients that exist only within a small selected volume requires many small accurately placed electrodes that may be controlled to work in unison. For example, it may be desirable to control three neighboring electrodes in a cooperative manner as a "triad" to produce desirable potential gradients. The ideal surface area for each electrode is on the order of 1,000 square microns or greater.

In the past it has been typical, due to the unsolved problem of accurate placement of the implant, for each electrode to be in the form of a ring encompassing the implant lateral circumference. At the current state of the art, these rings could be spaced apart longitudinally by a minimum of 750 μm. With this configuration, regardless of the orientation of the implant, a portion of each electrode faces the modiolar wall.

This configuration of electrodes, however, precludes any manipulation in the lateral dimension of the potential gradients. The potential gradients produced by the ring electrodes decrease monotonically with increasing lateral distance from the electrodes. In contrast, a high density array of electrodes spaced in a grid both laterally and longitudinally can produce precisely shaped lateral gradients with steep, non-monotonic slopes. The auditory neurons, arranged parallel to these lateral gradients, should respond more vigorously to such gradients than to the relatively shallow gradients producible by ring electrodes.

These electrodes must present as low a resistance as is possible to the emission of electrical current from their surfaces. Although the current to be applied is typically very small, current density is significant over the small electrode surface.

Furthermore, each electrode must be resistant to corrosion by the solution that it contacts.

A commonly used method for producing an electrode entails the removal of a small area of insulating dielectric material from a wire, creating an electrode in the form of an exposed wire surface. There are presently several techniques for performing this task, including AC electric corona arcing, direct heating, and plasma etching. These methods have not been completely satisfactory when applied to the biologically compatible dielectric materials which must be used for implants, either because they fail to leave a cleanly and accurately exposed electrode surface, or because the dielectric material forming the rim of the electrode does not adhere satisfactorily and tightly to the wire surface. Mechanical removal of the insulation is very time-consuming and has a high probability of damaging the wire.

Additionally, multiple conductor micro-electrode arrays have been produced using photolithographic-integrated circuit production techniques. These arrays, however, are too delicate for this application. Additionally, such microelectrode arrays lack conductors for connection to other electrical circuitry. This typically creates a potential failure point.

Techniques that do not involve the accurate removal of insulating dielectric material have also been used to create electrodes for use in a cochlear implant. These techniques are, however, more time and labor intensive than the techniques taught here. Furthermore, it would be virtually impossible to attempt to create an implant with the density of electrodes taught herein using the prior techniques.

Use of red light ruby lasers to pierce dielectric coatings in preparation of microelectrodes was described by M. J. Mela in 1965 in an article entitled "Microperforation with Laser Beam in the Preparation of Microelectrodes," published in *IEEE Transactions on Biomedical Engineering*, Vol. BME-13, No. 2, pp. 70–76. Unfortunately the use of this type of laser leaves remnants of dielectric coating on the metal surface of the electrode. These remnants interfere with the electrode's ability to emit electrical current. That is, before the present invention it has not been known how to remove biologically compatible dielectric materials cleanly from a metal surface using a laser to produce well-defined, efficient electrodes.

In addition, the helical shape of the cochlea makes it very difficult to place an implant so that it reaches the most remote portion of the scala tympani. Ideally the implant should extend to within 5 mm of the distal terminus of the 32 mm long scala tympani. The preferred location is at the modiolar wall of the scala tympani, which is adjacent to the auditory nerve cells. Pre-shaped cores, shaped insulators with extensions to force the implant to the inner wall, and spiralled implants have all been tried.

The complexity of the shape of the scala tympani, however, a helical structure that turns more tightly at the apex and tapers inward, presents a very difficult challenge not yet sufficiently answered. Complicating the problem is the possibility of damage either to the scala tympani or the implant during the insertion process. The techniques heretofore used have generally not proven adequate to allow the safe yet deep insertion of an implant.

SUMMARY OF THE INVENTION

An object of the present invention is, therefore, to provide a novel multi-electrode cochlear implant.

Another object of the present invention is to provide a multi-electrode cochlear implant that may be economically produced.

A further object of the present invention is to provide a multi-electrode cochlear implant that includes electrodes with an improved capability for emitting current.

Yet another object of the present invention is to provide a multi-electrode cochlear implant having electrodes formed and placed with great precision and accuracy.

Still another object of the present invention is to provide a multi-electrode cochlear implant that may be inserted into more complete and beneficial contact with the cochlea than was heretofore generally achievable.

Still another object of the present invention is to provide a high density multi-electrode cochlear implant in which the electrodes are configured not only longitudinally along the length of the implant but are also arranged laterally at separate locations along the circumference of the implant.

One aspect of the present invention is a multi-electrode cochlear implant comprising a plurality of fine wires electrically insulated from one another and held together about a flexible insulating tube by a quantity of a dielectric material. Each electrode comprises a small area of a particular wire where the dielectric materials have been removed by a laser beam. The laser beam also seals the dielectric material to the wire by heating around the periphery of the electrode. The laser beam may also be controlled to heat the metal surface to the point where it is roughened, thereby increasing the surface area and the current emitting capability of the electrode.

To further increase the current emitting capability of the electrode, a further layer of conductive metal, such as platinum black, may be deposited and electrically connected with the electrode in such a manner that its surface is particularly rough.

In a separate aspect of the present invention, a shape memory material core, such as nitinol, which is comprised of substantially 50% nickel and 50% titanium, is be placed inside the core of a cochlear implant. Alternatively, a different metal alloy or a shape memory polymer may be used. This type of material may be formed so that at above a particular temperature it assumes a particular shape. In this case it is formed so that it will assume a shape that will keep it into contact with the interior or modiolar wall of the scala tympani at body temperature.

In an additional separate aspect of the present invention, the shape memory is heated electrically by passing electric current through the shape memory material or adjacent heating elements. This permits a more precise control of the shape of the implant during the insertion process.

Alternatively, the insulating tube about which the wires are wrapped may provide a lumen through which instruments or a guide wire may be extended to aid in the implant insertion process. It would also be possible to have the tube filled largely with shape memory material, but to leave empty a large enough cross-sectional area to allow the insertion of a guide wire.

In one embodiment of the invention a second layer or valence of wires coaxially surrounds a first layer of wires. In this embodiment, the first layer of wires or valence protrudes beyond the terminus of the second layer of wires to provide a stepwise approximation of the tapering of the scala tympani. In like manner, additional wire layers may be included.

A considerable advantage of the production technique described herein is that it yields the ability to create an implant with electrodes that are laterally separated from each other. This yields an increased ability to control precisely the amplitude of nerve stimulation.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

FIG. 10 is a side view of an additional preferred embodiment of the shape memory core assembly 68 of FIG. 8.

FIG. 11 is a cross-sectional view of an a further additional preferred embodiment of the shape memory material core assembly 68 of FIG. 8 taken at the same cross-sectional cut as shown in FIG. 8.

FIG. 12 is a cross-sectional view of yet another additional preferred embodiment of the shape memory material core assembly 68 of FIG. 8 taken at the same cross-sectional cut as shown in FIG. 8.

DETAILED DESCRIPTION OF THE PREFERRED EMBODIMENT

Figure 1:
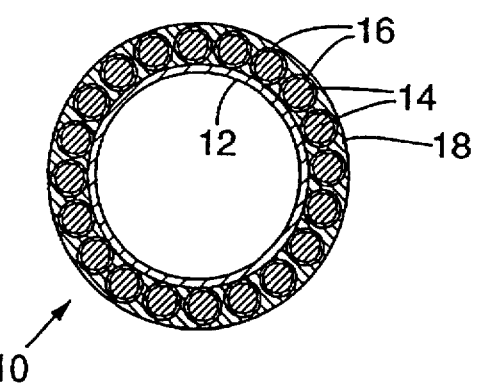
FIG. 1 is a greatly expanded cross-sectional view of a multi-electrode cochlear implant according to the present invention.
Figure 2:
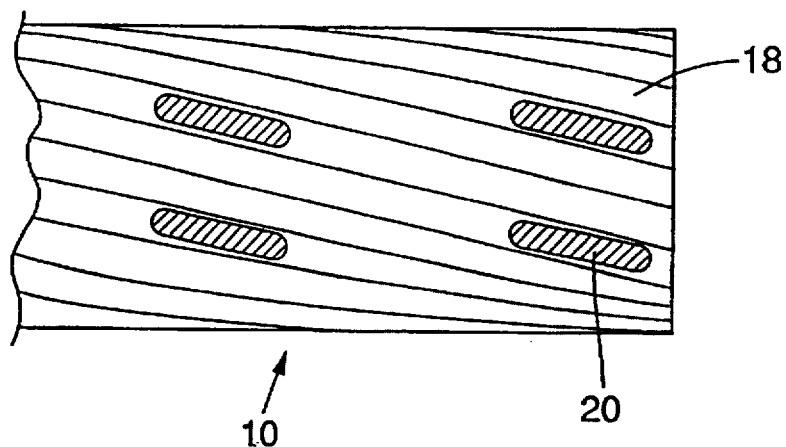
FIG. 2 is a greatly expanded side view of a portion of implant of FIG. 1, showing some electrodes.

A biologically implantable multi-electrode cochlear implant 10, shown in FIGS. 1–3, 7 and 8 is centered about a thin-walled tube 12. Several extremely fine wires 14, for example, twenty platinum or platinum alloy wires of American Wire Gauge 50, having a wire diameter of approximately 25 μm (0.001 inch), insulated from one another by suitable individual coatings 16 of flexible dielectric material are wrapped around the thin walled tube 12 in a helical serving in which the individual fine wires 14 lie neatly alongside one another without overlapping. A comprehensive coating 18 of dielectric material covers and binds together this structure. Dielectric materials which are usable for coating 18 must be biocompatible elastomers with good insulating properties such as silicone, a coating of which is available from PI Medical, 16125 S.W. 72 Avenue, Portland, Ore. 97224, under the trademark Silablate®. Also appropriate for this use are fluorocarbons, polyimides or derivatives thereof, epoxies, enamel, or a polymer of parachloroxylylene, such as that available from Union Carbide Corporation under the trademark Parylene-®.

Comprehensive coating 18 is very thin and completely covers the implant, including the distal end. If Parylene-® is used, for example, it may be vacuum deposited on the surface of wire coatings 16 and have a thickness of 6–12 µm.

An active electrode 20 with typical dimensions 20 by 100 µm is created by removing the coatings of dielectric material 16, 18 by exposing them to an ultraviolet laser beam focused with a lens to a 20 µm diameter spot and scanned over the desired 100 µm length.

A frequency-quadrupled YAG (FQY) laser operated in the fundamental transverse electromagnetic ($TEM_{00}$) mode is suitable to ablate portions of the coating 16, 18. Such a laser has a 266 nanometer wavelength which is in the ultraviolet (UV) range. Typically, this laser is Q-switched at around 1–20 Khz, producing a 40 ns full-width half maximum (FWHM) pulse, producing a fluence of approximately 10–50 joules/$cm^2$, at an average power of 300–400 milliwatts.

It has been found that such a highly focused laser beam in the ultraviolet frequency band is readily absorbed by dielectric coatings 16, 18 and is absorbed by the surfaces of wires 14, which are typically made of platinum or a platinum alloy, with the result that coatings 16, 18 are both photoablated by the laser beam and vaporized through contact with the heated metal which quickly reaches temperatures exceeding 1000° C. This process removes coatings 16, 18 cleanly from wire 14 surfaces.

The FQY laser beam spot can be moved under computer software control to scan coatings 16, 18 to remove them from the conductor body. Scanning control can be provided, for example, by equipment designed to control lasers for use in manufacture of integrated circuit products, such as is available from Electro Scientific Industries, Inc., of Beaverton, Ore. Preferably, the UV laser is utilized together with exhaust and positive gas pressure systems to keep debris away from the focusing lens and the area where dielectric material is being ablated. Operation of the laser at the powers mentioned above provides an effective range of etch depths of approximately 1–50 microns in silicone, polyamide or Parylene-® (polypara-chloroxylylene).

Coatings 16, 18 rimming the active electrodes are also heated by the effects of the UV laser beam. As a result, this portion of coatings 16, 18 melts, fuses together, solidifies and forms a strong adhesive bond with underlying wire 14. This bond hermetically seals the rest of the wire 14 from electrode 20 opening and serves to, among other valuable functions, reduce crosstalk among wires 14.

The spacing and orientation of the active electrodes 20 corresponding to the several fine wires 14 may be chosen as desired consistent with the pitch of the helical wrapping of fine wires 14 about the core. When desired, active electrode 20 may be spaced radially about implant 10, or they may be spaced longitudinally in a helical arrangement along the implant 10, separated more or less from one another as determined by the number of adjacent ones of the fine wires 14 which are skipped between consecutive active contact sites 20 defined along the implant 10.

Figure 3:
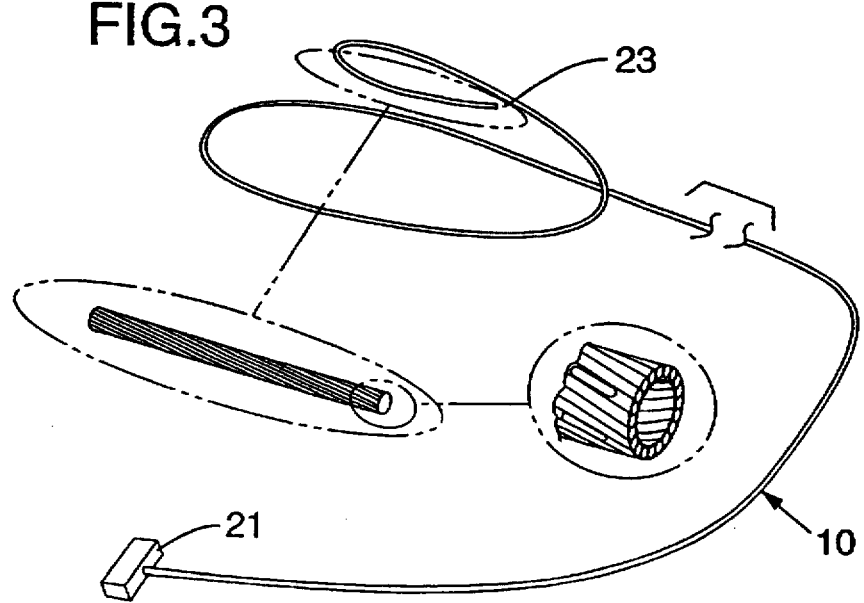
FIG. 3 is an expanded perspective view of the implant of FIG. 1 configured in the shape of the scala tympani.

FIG. 3 shows a cochlear implant configured in the shape of the scala tympani. A proximal end connector 21 of implant 10 is used to connect implant 10 to supporting electrical cabling, which in turn is to be connected with an implant driving device. The distal end 23 of the implant is adhered together with the comprehensive dielectric material 18.

Figure 4:
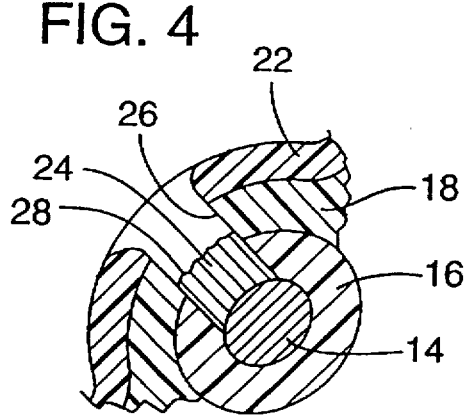
FIG. 4 is a greatly expanded cross-sectional view of an electrode of the multi-electrode cochlear implant of the present invention.

Further metal may be electrophoretically deposited into the electrodes 20. FIG. 4 shows an electrode 20 of the preferred embodiment of the present invention. An optional third layer 22 of dielectric material has been added here for further protection. More significantly, platinum black 24 has been electrophoretically deposited on wire 14 surface in electrode opening 26. The rough surface 28 of this material serves to increase the surface area and therefore reduce resistance of the electrode 20 to the emission of electrical current.

Another potential coating for an electrode 20 surface is comprised of iridium with a surface layer of iridium oxide. Alternatively iridium alone can be applied. Iridium is conductive and the surface layer of iridium oxide provides a large current releasing capacity. One method of producing such a coating can be initiated after the application of the second dielectric material 18. At this point, a layer of water soluble "resist" material, familiar to skilled persons in the art of integrated circuit fabrication, is applied to the implant. Next, the electrodes are formed by application of the laser beams, which removes the "resist" material as well as the dielectric coatings 16, 18. The implant is then placed in a chamber and sputtered with iridium. A surface layer of iridium oxide may also be sputtered on at this point. After removing the underlying resist material layer by submerging the implant in a dissolving solution, the only iridium remaining on the implant is that on the electrodes 20.

As an alternative to sputtering, cyclic voltametry can be used for creating the layer of iridium oxide on the iridium coating. In this method, the implant, after the steps of creating electrodes with a laser beam, is submerged in a bath of electrolytes and subjected to a voltage that causes the iridium to oxidize rapidly.

Figure 5:
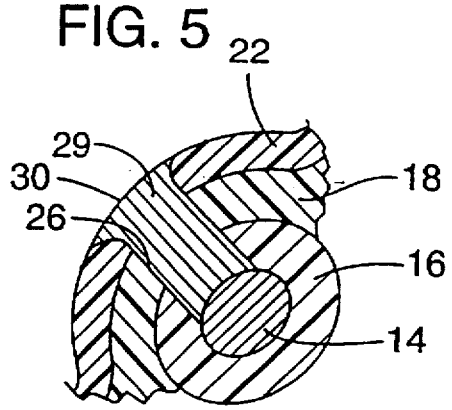
FIG. 5 is a greatly expanded cross-sectional view of an electrode of an alternative embodiment of the multi-electrode cochlear implant of the present invention.
Figure 6:
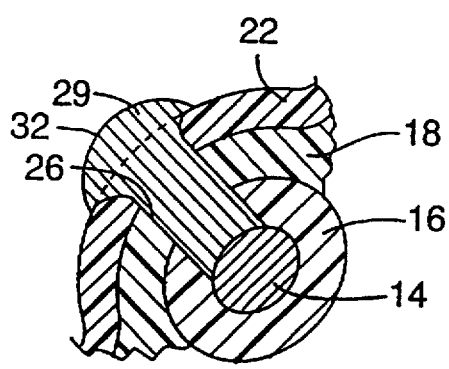
FIG. 6 is a greatly expanded cross-sectional view of an electrode of another alternative embodiment of the multi-electrode cochlear implant of the present invention.

FIGS. 5 and 6 show the electrode opening 26 filled to an even surface 30 (FIG. 5) or overfilled to a bulging surface 32 (FIG. 6) with either platinum or iridium 29.

Figure 7:
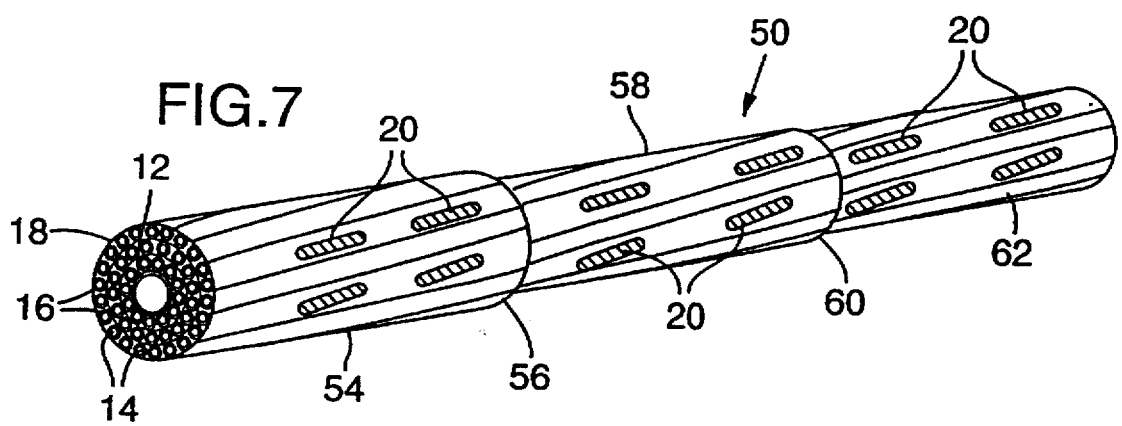
FIG. 7 is a greatly expanded perspective view of an alternative embodiment of the present invention.

FIG. 7 is a greatly expanded perspective view of an alternative embodiment of a cochlear implant 50 in which the thickness of implant 50 follows a stepwise approximation to a proportion of the width of the scala tympani. In this embodiment three layers or valences of wires are coaxially wound around each other. The outermost valence 54 includes a set of four electrodes 20 located slightly proximally of the distal termination 56 of valence 54. Typically the electrodes 20 are spaced approximately 300 µm apart longitudinally.

Note that for every longitudinal position of the electrodes 20 there are two electrodes 20 spaced apart laterally by about an eighth of a circumference (@100 µm). The lateral placement of electrodes serves the important function of allowing the lateral positioning and orientation of the potential gradients. This in turn permits a more precise control of the potential gradients.

In the interior of valence 54 resides a second valence 58. Second valence 58 continues in the distal dimension past the distal terminus 56 of outermost valence 54. All of the electrodes 20 of second valence 58 are located in this portion. The innermost valence 62 protrudes approximately 1 cm past the distal terminus 60 of second valence 58. The electrodes 20 of innermost valence 62 are located in this protrusion. Not only are more wires and therefore more electrodes 20 possible in this embodiment but the gradual stepwise narrowing of the implant mirrors the narrowing of the cochlea.

The distal section of the preferred embodiment includes a core made of a shape memory material, such as nickel-titanium alloy made of substantially 50% nickel and 50% titanium. This material has the unusual property that it may be prepared in such a manner that it will, upon reaching some predetermined temperature, assume a predetermined shape. Nitinol having specified transition temperature characteristics may be obtained from Shape Memory Applications, Inc. 2380 Owen Street, Santa Clara, Calif. 95054.

At below human body temperature the shape memory material would be quite malleable and flexible, allowing it to be inserted a preliminary distance. As it is inserted further, warming up in the process, it will begin to curve allowing for easier insertion through the curves of the scala tympani. Finally, when it is completely installed and warmed to body temperature, it will assume the shape of the scala tympani but in a form tight enough so that it will contact the interior modiolar wall where the auditory neurons have their receptive termini. For this embodiment, nitinol having a transition temperature at approximately human body temperature is used.

Figure 8:
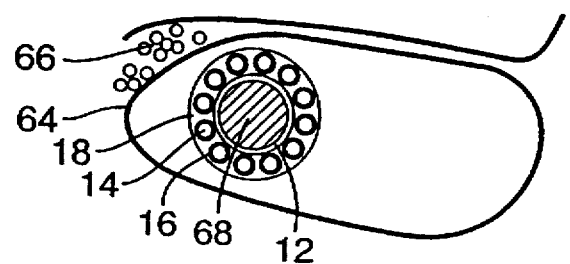
FIG. 8 is a greatly expanded cross-sectional view of the implant of FIG. 1 inside the scala tympani.

FIG. 8 is a greatly expanded cross-sectional view of the implant in the scala tympani. In this depiction the implant is held close to the modiolar wall 64 and the nearby nerve cells 66 by the shape memory core assembly 68.

FIG. 8 shows shape memory core assembly 68 as a simple undifferentiated element. FIGS. 9a–12 show the details of various preferred embodiments of shape memory core assembly 68. For ease of description these are shown individually, isolated from the rest of the structure of cochlear implant 10. Any of the preferred embodiments of shape memory core assembly 68 shown in FIGS. 9a–12 would fit inside tube 12 of cochlear implant 10 as shown in FIG. 1, FIG. 7 or FIG. 8.

Figure 9A:
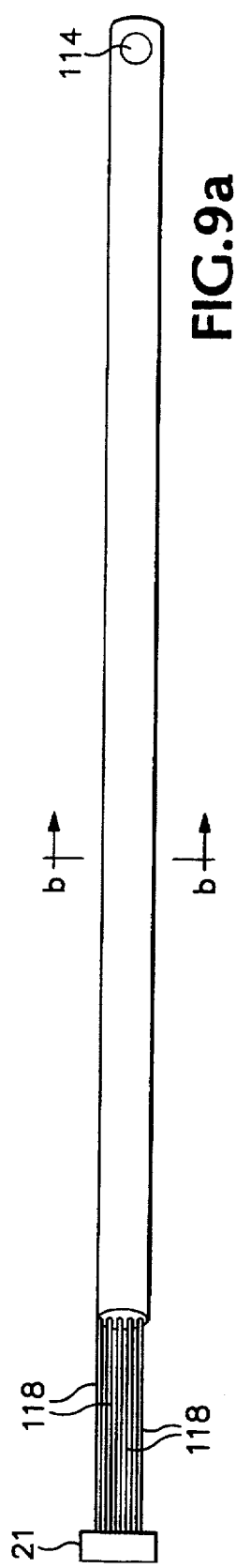
FIG. 9a is a side view of a preferred embodiment of the shape memory core assembly 68 of FIG. 8.
Figure 9C:
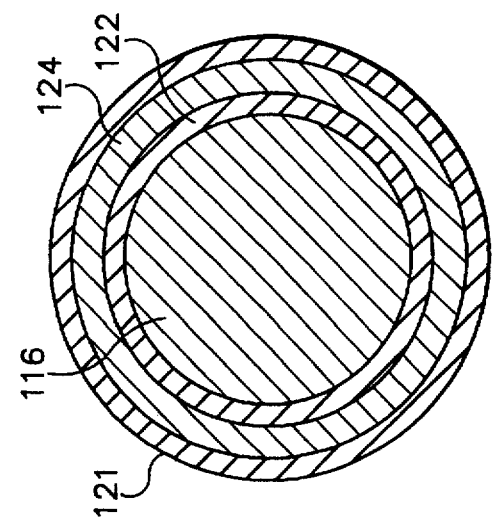
FIG. 9c is a cross-sectional view of an additional preferred embodiment of the shape memory core assembly of FIG. 9a taken along line b—b.
Figure 9B:
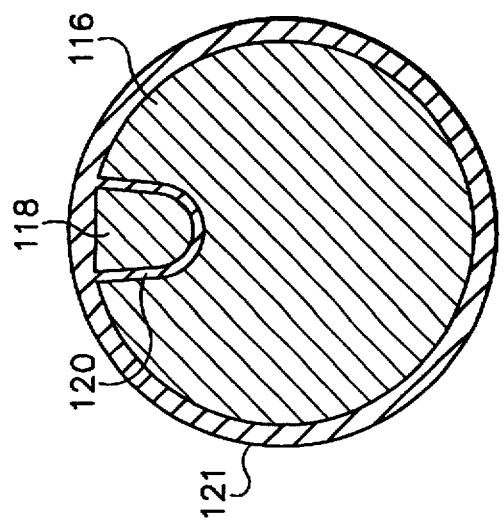
FIG. 9b is a cross-sectional view of a preferred embodiment of the shape memory core assembly of FIG. 9a taken along line b—b.

FIGS. 9a–9b collectively show a single preferred embodiment of shape memory core assembly 68. Connector 21 (which is connected to additional portions of implant 10, not shown in FIGS. 9–12) is electrically connected to a connection point 114 both through a shape memory material core 116 and through an electrical conductor or conductors 118. Typically, electrical conductor 118 is connected with an active terminus of connector 21 and shape memory material core 116 is connected with a grounded terminus of connector 21, although it is possible to reverse these connections. Electrical conductor 118 is insulated from shape memory material core 116 by insulative coating 120, except at connection point 114 where conductor 118 and core 116 are in electrical contact. Shape memory material core 116 is sheathed in an exterior insulative coating 121.

FIGS. 9a and 9c collectively show an additional preferred embodiment for shape memory core assembly 68. In this embodiment, shape memory material core 116 is surrounded by annular insulative coating 122 and an annular electrical conductor 124. Similar to the embodiment shown in FIGS. 9a and 9c shape memory material core 116 and annular electrical conductor 124 are electrically connected at connection point 114.

When heated to a temperature of between 35° C. (95° F.) and 45° C. (113° F.) shape memory material core 116 assumes a coil shape that is slightly tighter than the coiling of the scala tympani. The slightly tighter coiling causes cochlear implant 10 to press against the modiolar wall of the scala tympani, thereby permitting superior stimulation of the auditory nerve endings. Core 116 retains this coil shape at temperatures of approximately 37° C. (98.6° F.).

As a practical matter, nitinol transitions over a range of temperatures, with a more complete transition taking shape at the higher temperatures of the transition range. The insertion process is facilitated by controlling the degree of transition effected at different stages of the insertion process.

FIG. 3 shows cochlear implant 10 coiled into the shape of the scala tympani. The task of inserting cochlear implant 10 is a challenge which sometimes results in abrasions to the wall of the scala tympani. According to the method of the present invention, cochlear implant 10 is gradually warmed as it is inserted so that it may be more easily inserted. The reader may note that the scala tympani is progressively more tightly coiled toward its interior extremis. Therefore, as the shape of cochlear implant 10 is progressively deformed during the insertion process, distal end 26 of cochlear implant 10 is coiled to a degree which generally matches the portion of the scala tympani through which distal end 26 is being moved.

FIG. 10 shows an embodiment in which different portions of the length of shape memory material core 116 may be heated and thereby deformed, independently of one another. This permits a precise deformation of cochlear implant 10 to match the portion of the scala tympani through which implant 10 is being inserted.

In greater detail ground contact point 126 grounds a proximal end 128 of shape memory material core 116 through a ground conductor 130. A set of active signal conductors 132 and active signal contact points 134 permit the independent application of electrical current and thereby independent heating and deformation of portions of shape memory material core 116. Any one of active signal conductors 132 may be grounded to permit the heating of a distal portion without causing the heating of the more proximal portions.

Conductors 130 and 132 may comprise gold, platinum, or silver wires or alloys of these metals and other metals, such as iridium; conductive epoxies or conductive paints. Shape memory material core 116 is made of nitinol, as discussed previously or other metallic alloys (described in Table 1) or polymers as discussed previously. Shape memory polymer material made to meet provided specifications may be obtained from Memory Corporation of 57 Commerce Drive, Brookfield, Conn. 06804.

Nitinol transitions from a highly passively deformable state at low temperatures (Martensite form) to a much less deformable state (Austenite form) at higher temperatures. A shape transition temperature in the range of 35° C. to 45° C. is used in the embodiments of FIGS. 9a–12 to allow electric control of the warming process.

TABLE 1

| Alloy | Composition | Transformation Temperature Range | |
|---|---|---|---|
| | | °C. | °F. |
| Au—Cd | 46.5/50 at % Cd | 30 to 100 | 85 to 212 |
| Cu—Al—Ni | 14/14.5 wt % Al 3/4/5 wt. % Ni | −140 to 100 | −220 to 212 |
| Cu.Zn.X (X=Si, Sn, Al) | a few wt. % of X | −180 to 200 | −290 to 390 |
| In—Ti | 18/23 at % Ti | 60–100 | 140 to 212 |
| Ni—Al | 36/38 at % Al | −180 to 100 | −290 to 212 |
| Ni—Ti | 49/51 at % Ni | −50 to 100 | −60 to 230 |
| Mn—Cu | 5/35 at % Cu | −250 to 180 | −420 to 355 |
| Fe—Mn—Si | 32 wt % Mn, 6 wt % Si | −200 to 150 | −330 to 300 |

An additional preferred embodiment of shape memory core assembly 68 is shown in FIG. 11. In this embodiment a shape memory material core 216 is surrounded by a set of heating elements 218. Heating elements 218 warm shape memory material core 216 to the transition temperature range 35°–45° C. (95° F.–113° F.). Heating elements 218 may be U-shaped with each element extending from the proximal end connector 21 of assembly 68 to the distal end 23 and back to proximal end connector 21. Alternatively, heating elements 218 may actually comprise only a few elements 218 (or even just one element 218), each element 218 extending back and forth between proximal end connector 21 and distal end 23 many times. Heating elements 218 may be fashioned so that each heating element 218 heats a different longitudinal portion of shape memory material core 218, for more precise control of the insertion process. FIG. 12 shows a variant of the embodiment of FIG. 11, with a heating element sheath 220 surrounding and, upon command, warming shape memory material core 216. Electrical lead 222 is insulated from shape memory material core 216 and heating element sheath 220 by an insulative coating 224. Electrical lead 222 is connected to heating element sheath 220 at the distal end of shape memory core assembly 68. Electrical lead 222 either provides a ground return or a stimulating voltage for heating element sheath 220 with the converse stimulating voltage or ground return for heating element sheath 220 found on the proximal end of shape memory core assembly 68. One advantage of the embodiments shown in FIGS. 11 and 12 is that shape memory material core 216 may be comprised of materials that are not conductive, such as shape memory polymers.

Heating elements 218 and heating element sheath 220 may be made out of any of the great multiplicity of materials that are conductive enough to bear current and are resistive enough to be warmed up by it. Many metals and alloys are available for this purpose. Conductive polymers that may be applied in liquid form and set are of particular interest with respect to heating element sheath 220.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A generally flexible cochlear implant comprising:

a core of moderately conductive shape memory material that has been pretreated to transform into the shape of the scala tympani at a temperature level greater than 35° C. (95° F.) and to subsequently remain in the shape of the scala tympani at a temperature of approximately 37° C. (98.6° F.);

a set of electrodes disposed about the core;

an electrical connector;

a first set of electrical conductors electrically connecting the electrical connector to the shape memory material core for warming the shape memory material core to its transition temperature by passing an electric current through it;

a second set of electrical conductors electrically connecting the set of electrodes to the connector.

2. The cochlear implant of claim 1 having a proximal end and a distal end and wherein the first set of electrical conductors includes a first electrical conductor connected to the shape memory material core at a first point and a second electrical conductor connected to the shape memory material core at a second point distal to the first point.

3. The cochlear implant of claim 2 wherein the first set of electrical conductors additionally includes a third electrical conductor connected to the shape memory material core at a third point distal to the second point.

4. The cochlear implant of claim 2 wherein the first electrical conductor comprises shape memory material.

5. The cochlear implant of claim 1 wherein the core of shape memory comprises nitinol.

6. A generally flexible cochlear implant comprising:

a core of moderately conductive shape memory material that has been pretreated to transform into the shape of the scala tympani at a temperature level greater than 35° C. (95° F.) and to remain in the shape of the scala tympani at a temperature of approximately 37° C. (98.6° F.);

a set of electrodes disposed about the core;

an electrical connector;

at least one electrical heating element having both a ground connection and an active connection and being electrically connected to the electrical connector by way of both said ground connection and said active connection for warming the shape memory material core to its transition temperature by passing an electric current through each heating element;

a set of electrical conductors electrically connecting the set of electrodes to the connector.

7. A method of placing a set of electrodes into contact with the modiolar wall of a human subject, comprising:

providing a cochlear implant having:

a shape memory material core that has been pretreated to transform into the shape of the scala tympani at a temperature range of approximately 35° C. (95° F.) to 45° C. (113° F.) and to remain in the shape of the scala tympani at a temperature of approximately 37° C. (98.6° F.);

a set of electrodes disposed about the core;

an electrical connector; and a first set of electrical conductors electrically connecting the set of electrodes to the connector;

inserting the cochlear implant through the ear canal of the human subject into the opening of the scala tympani of the human subject;

warming the shape memory material core to a temperature level greater than 35° C. (95° F.); and inserting the cochlear implant into contact with the modiolar wall, thereby placing the set of electrodes into contact with the modiolar wall.

8. The method of claim 7 further including the step of placing the cochlear implant into close proximity with the walls of the scala tympani of the human subject and thereby permitting the conductance of heat from the walls of the scala tympani of the human subject into the cochlear implant and, more specifically, the shape memory material core, to warm the shape memory material core to a temperature level of greater than 35° C.

9. The method of claim 7 wherein the shape memory material core is moderately conductive and the cochlear implant further comprises a second set of electrical conductors electrically connecting the electrical connector to the shape memory material core and further comprising the step of passing an electrical current through the shape memory material core, to warm it.

10. The method of claim 9 further including the step of inserting the cochlear implant through the curves of the scala tympani during the step of passing an electrical current through the shape memory material core, to warm it.

11. The method of claim 7 wherein the cochlear implant further comprises an electrically conductive heating element having a grounded connection point and an active connection point and being laterally adjacent to the shape memory material core and electrically connected to the electrical connector through both the grounded connection point and the active connection point and further comprising the step of passing an electric current through the heating element to warm the shape memory material.

12. The method of claim 11 wherein the cochlear implant has a proximal end and a distal end and the second set of electrical conductors comprise a first electrical conductor connected to the shape memory material at a first point, a second electrical conductor connected to the shape memory material at a second point distal to the first point and a third electrical conductor connected to the shape memory material at a third point distal to the second point and wherein warming the shape memory material includes:

passing electric current between the third point and the second point of the shape memory material; and passing electric current between the second point and the first point of the shape memory material.

13. The method of claim 12 further including the steps of inserting the cochlear implant into the scala tympani during the step of passing electric current between the third point and the second point and inserting the cochlear implant further into the scala tympani during the step of passing electric current between the second point and the first point.

14. The method of claim 7 wherein the cochlear implant further comprises an electrically conductive heating element having a grounded connection point and an active connection point and being laterally adjacent to the shape memory material core and electrically connected to the electrical connector through both the grounded connection point and the active connection point and further including the step of passing an electric current through the heating element to warm the shape memory material.

15. The method of claim 14, wherein the cochlear implant further comprises additional electrically conductive heating elements that are longitudinally sequenced along a portion of the length of the shape memory material core and further comprising the step of selectively warming the longitudinally sequenced heating elements of the shape memory material core.

* * * * *

UNITED STATES PATENT AND TRADEMARK OFFICE
CERTIFICATE OF CORRECTION

PATENT NO : 5,800,500
DATED : September 1, 1998
INVENTOR(S) : Spelman et al.

It is certified that error appears in the above-identified patent and that said Letters Patent is hereby corrected as shown below:

Col 5, line 4         Delete [Parylene-®]
                      Insert --Parylene-C®

Col 5, line 6         Delete [Parylene-®]
                      Insert --Parylene-C®

Col 5, line 43        Delete [Parylene-®]
                      Insert --Parylene-C®

Signed and Sealed this

Twenty-eighth Day of December, 1999

Attest:

Q. TODD DICKINSON

*Attesting Officer*    *Acting Commissioner of Patents and Trademarks*